US00PP08197P

United States Patent [19]

Bradford et al.

[11] Patent Number: Plant 8,197

[45] Date of Patent: Apr. 6, 1993

[54] NECTARINE TREE (BIG JUAN)

[76] Inventors: Lowell G. Bradford, 12439 E. Savana Rd.; Norman G. Bradford, 11875 E. Savana Rd., both of Le Grand, Calif. 95333

[21] Appl. No.: 833,055

[22] Filed: Feb. 10, 1992

[51] Int. Cl.[5] ..... A01H 5/00
[52] U.S. Cl. ..... Plt./41.3
[58] Field of Search ..... Plt./41.3

[56] References Cited

U.S. PATENT DOCUMENTS

P.P. 3,165 5/1972 Anderson ..... Plt. 41.3
P.P. 5,454 4/1985 Bradford ..... Plt. 41.1

*Primary Examiner*—James R. Feyrer

[57] ABSTRACT

The present invention relates to a nectarine tree and more particularly to a new and distinct variety broadly characterized by a large size, vigorous, hardy, productive and regular bearing tree. The fruit matures under the ecological conditions described approximately the second week in June, with first picking on Jun. 13, 1991. The fruit is uniformly large in size, excellent in flavor, attractively globose in shape, freestone in type, very firm in texture, and full red in skin color. The variety was developed as a hybridized seedling from the selected seed parent of Red Diamond Nectarine (U.S. Plant Pat. No. 3,165) and an unnamed nectarine seedling as the selected pollen parent.

1 Drawing Sheet

BACKGROUND OF THE VARIETY

In a continuing effort to improve the quality of shipping fruits, we, the inventors, typically hybridize a large number of nectarine, peach, plum, apricot, and cherry seedlings each year. The present invention relates to a new and distinct variety of nectarine tree, which has been denominated varietally as "Big Juan". The present variety was hybridized in 1984 by us in a cultivated area of our experimental orchard at Bradford Farms near Le Grand, Calif., in Merced County (San Joaquin Valley). This hybrid seedling resulted from using Red Diamond Nectarine (U.S. Plant Pat. No. 3,165) as the selected seed parent and an unnamed nectarine seedling as the selected pollen parent. Subsequent to origination of the present variety of nectarine tree, we asexually reproduced it by budding and grafting, and such reproduction of plant and fruit characteristics were true to the original plant in all respects.

The fruit produced by the present variety is most similar to that of the May Diamond Nectarine (U.S. Plant Pat. No. 5,454) by being full red in color, by maturing in June, and by being freestone in type, but is distinguished therefrom and an improvement thereon by producing fruit that is larger in size, that is purely yellow to the stone in flesh color, and that ripens 7 days earlier.

The present variety is similar to its selected seed parent, the Red Diamond (U.S. Plant Pat. No. 3,165), in fruit appearance by being a full red colored freestone nectarine with excellent firmness, but is distinguished therefrom and an improvement thereon by producing fruit that ripens 28 days earlier.

DRAWING

The accompanying photograph exhibits four whole fruits positioned to display the characteristics of the skin color and form, one fruit divided transversely to the suture plane to reveal the flesh and stone, and typical leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of hard eating ripe on Jun. 16, 1991. All major color code designations are by reference to the Inter-Society Color Council, National Bureau of Standards. Common color names are also used occasionally.

TREE

Size: Large.
Vigor: Vigorous.
Growth: Spreading and dense.
Form: Vase formed.
Hardiness: Hardy.
Production: Productive.
Bearing: Regular bearer.
Trunk:
- *Size.*—Medium.
- *Texture.*—Medium.
- *Bark color.*—Dark yellowish brown [78. d.yBr].
- *Lenticels.*—Numerous. Color: Light yellowish brown [76. l.yBr]. Size: ⅛" to ¼", [3.2–6.4 mm.].

Branches:
- *Size.*—Medium.
- *Texture.*—Medium.
- *Color.*—1st year wood topside: Light grayish red [18. .gy.R]. 1st year wood underside: Brilliant yellow green [116. brill.YG]. Older wood: Grayish brown [61. gy.Br].
- *Lenticels.*—Numerous, very small.

Leaves:
- *Size.*—Large. Average length: 6½" [165.1 mm.]. Average width: 1⅝" [41.3 mm.].
- *Thickness.*—Medium. *Form.*—Elliptical. *Apex.*—Acuminate. *Base.*—Acute. *Surface.*—Smooth.

*Color.*—Dorsal surface: Dark olive green [126 .d.d. Ol01G]. Ventral surface: Moderate yellow green [120. m.YG].

*Margin.*—Finely serrate.

*Venation.*—Pinnately net veined.

*Petiole.*—Average length: 7/16" [11.1 mm.]. Average thickness: 1/16" [1.6 mm.]. Dorsal color: Moderate olive green [125. m. Ol G.]. Ventral color: Light yellow green [119. 1 .YG].

*Stipules.*—Numerous. Length: 3/16" to ¼"[4.8-6.4 mm.].

*Glands.*—Numbers: 2, 3, or 4 per leaf.

Position: Mostly oppositely positioned on petiole and base of blade, but slightly offset. Size: Medium. Form: Reniform. Color: Moderate olive green [125. m.Ol 01G].

Flower buds:

*Hardiness.*—Hardy.

*Size.*—Medium.

*Length.*—Medium.

*Form.*—Free.

*Surface.*—Pubescent.

Flowers:

*Blooming period.*—Medium as compared with other varieties.

*Size.*—Small.

*Color.*—Moderate pink [5. m.Pk].

FRUIT:

Maturity when described: Firm but eating ripe, Jun. 16, 1991.

Date of first picking: Jun. 13, 1991.

Date of last picking: Jun. 21, 1991.

Size: Uniform, large.

*Average diameter axially.*—2½" 63.5 mm.].

*Average traversely in suture plane.*—2½" [63.5 . mm.]

Form: Uniform, symmetrical, globose with some slight truncation at the base.

*Longitudinal section form.*—Round.

*Transverse section through diameter.*—Round.

Suture: An inconspicuous shallow line extending from the base to the apex, becoming deeper toward both the base and apex, extending to beyond the pistil point.

Ventral surface: Rounded, lipped slightly on both sides.

Lips: Slightly unequal.

Cavity: Flaring, circular, suture showing on both sides.

*Depth.*—⅜" [9.5 mm.].

*Breadth.*—⅝" [15.9 mm.].

Base: Slightly truncate, with stem markings typical.

Apex: Rounded.

Pistil point: Some apical and some oblique, very short in length.

Stem: Medium.

*Average length.*—⅜"[9.5 mm.].

*Average width.*—3/16" [4.8 mm.].

Skin:

*Thickness.*—Medium.

*Texture.*—Medium.

*Tenacity.*—Tenacious to flesh.

*Tendency to crack.*—None observed as of yet.

*Color.*—Dark red [16. d.R] over a deep red [13. deep R] background with brilliant orange yellow [67. brill.OY] stem marks typical.

Flesh:

*Color.*—Brilliant yellow [83. brill.Y] to the stone.

*Surface of pit cavity.*—Covered with light yellow [86. l.Y]fibers.

*Amygdalin.*—Moderate.

*Juice.*—Abundant, rich.

*Texture.*—Very firm, tough, crisp.

*Fibers.*—Abundant, fine.

*Ripens.*—Evenly.

*Flavor.*—Acidic, but sweet.

*Aroma.*—Slight.

*Eating Quality.*—Very good.

STONE

Type: Freestone.

Form: Oval to oblong.

Base: Straight.

Apex: Acute.

Sides: Equal.

Surface: Irregularly furrowed toward the apex and pitted toward the the base.

Ridges: Jagged toward the base.

Color: Light yellowish brown [76. l.yBr].

Pit wall: ¼" [6.4 mm.] thick.

Tendency to split: None observed.

Kernel:

*Form.*—Oval.

*Taste.*—Sweet.

*Viable.*—Yes.

*Average width.*—9/16" [14.3 mm.].

*Average length.*—¾" [*19.1* mm.].

*Color.*—Pale yellow [89. p.Y] when first cracked.

*Pellicle color.*—Grayish yellow [90. gy.Y].

*Amygdalin.*—Scant.

USE

Market: Fresh and long distance shipping.

Keeping quality: Very good.

Shipping quality: Very good.

Resistance to insects: No unusual susceptibilities noted.

Resistance to diseases: No unusual susceptibilities noted.

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varyiung cultural practices.

We claim:

1. A new and distinct variety of nectarine tree, substantially as illustrated and described, which is most similar to May Diamond Nectarine (U.S. Plant Pat. No. 5,454) by producing early maturing, full red, freestone fruit but is distinguished therefrom and an improvement thereon by producing fruit that is larger in size, that is purely yellow to the stone in flesh color, and that ripens 7 days earlier.

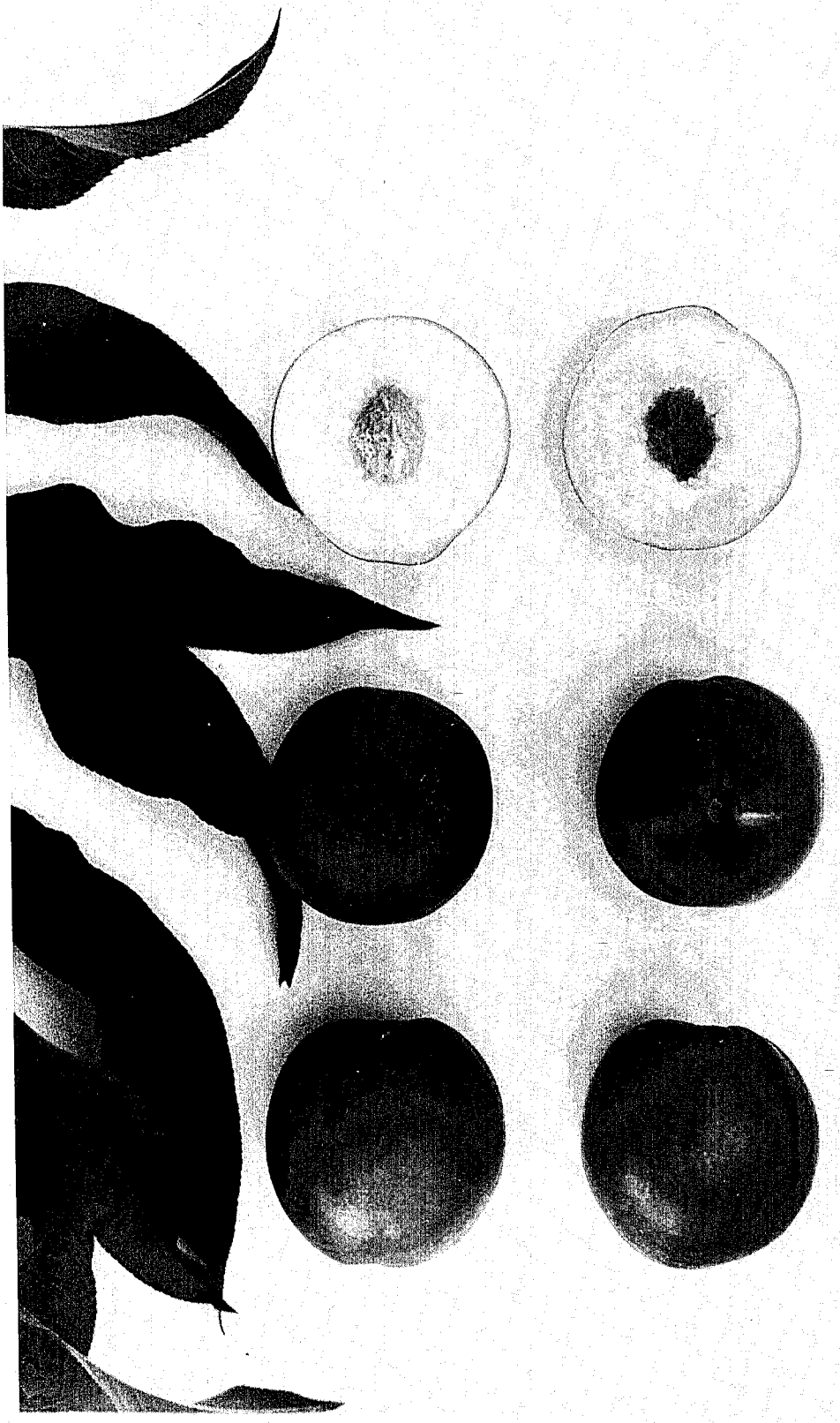

* * * * *